(12) United States Patent
Yamamoto et al.

(10) Patent No.: US 10,040,761 B2
(45) Date of Patent: Aug. 7, 2018

(54) BRANCHED HETERO POLYETHYLENE GLYCOL AND INTERMEDIATE

(75) Inventors: Yuji Yamamoto, Kanagawa (JP); Hiroki Yoshioka, Kanagawa (JP); Fumiaki Manabe, Kanagawa (JP)

(73) Assignee: NOF CORPORATION, Tokyo (JP)

( * ) Notice: Subject to any disclaimer, the term of this patent is extended or adjusted under 35 U.S.C. 154(b) by 378 days.

(21) Appl. No.: 13/167,777

(22) Filed: Jun. 24, 2011

(65) Prior Publication Data
US 2012/0077988 A1 Mar. 29, 2012

Related U.S. Application Data

(60) Provisional application No. 61/359,433, filed on Jun. 29, 2010.

(30) Foreign Application Priority Data

Jun. 25, 2010 (JP) ................ P2010-145383

(51) Int. Cl.
| | |
|---|---|
| C07D 207/452 | (2006.01) |
| C07D 209/48 | (2006.01) |
| C08G 65/26 | (2006.01) |
| C08G 65/331 | (2006.01) |
| C08G 65/333 | (2006.01) |
| C08G 65/334 | (2006.01) |
| G01N 33/543 | (2006.01) |

(52) U.S. Cl.
CPC ....... *C07D 207/452* (2013.01); *C07D 209/48* (2013.01); *C08G 65/2612* (2013.01); *C08G 65/3312* (2013.01); *C08G 65/3344* (2013.01); *C08G 65/33337* (2013.01); *C08G 65/33396* (2013.01); *G01N 33/54353* (2013.01); *C08L 2203/02* (2013.01)

(58) Field of Classification Search
None
See application file for complete search history.

(56) References Cited

U.S. PATENT DOCUMENTS

| | | | |
|---|---|---|---|
| 5,483,008 A | 1/1996 | Sakurai et al. | |
| 5,605,976 A | 2/1997 | Martinez et al. | |
| 6,362,254 B2 | 3/2002 | Harris et al. | |
| 6,875,841 B2 | 4/2005 | Sakanoue et al. | |
| 7,524,875 B2* | 4/2009 | Nakamoto et al. | 514/359 |
| 8,003,117 B2* | 8/2011 | Nakamoto et al. | 424/400 |
| 8,067,526 B2* | 11/2011 | Yoshioka et al. | 528/313 |
| 2003/0065134 A1 | 4/2003 | Sakanoue et al. | |
| 2005/0063936 A1 | 3/2005 | Yamasaki et al. | |
| 2006/0115450 A1* | 6/2006 | Nakamoto et al. | 424/78.38 |
| 2010/0056555 A1* | 3/2010 | Horak et al. | 514/283 |

FOREIGN PATENT DOCUMENTS

| | | |
|---|---|---|
| CN | 1400232 A | 3/2003 |
| EP | 1857462 A1 | 11/2007 |
| JP | 5279469 A | 10/1993 |
| JP | 7048449 A | 2/1995 |
| JP | 7048450 A | 2/1995 |
| JP | 11228685 A * | 8/1999 |
| JP | 2000001541 A | 1/2000 |
| JP | 2001519784 A | 10/2001 |
| JP | 2004149937 A * | 5/2004 |
| WO | 95/11924 A1 | 5/1995 |
| WO | 98/41562 A1 | 9/1998 |
| WO | 02060978 A1 | 8/2002 |
| WO | 03/040211 A2 | 5/2003 |
| WO | WO 2005000360 A2 * | 1/2005 |

OTHER PUBLICATIONS

Yamamoto et al. "Novel branched Poly(ethylene glycol) delivatives for bioconjugate" Polymer Preprints Published by ACS 2009, 50(1), 161-162.*
Yongdoo Park, Matthias P. Lutolf, Jeffrey A. Hubbell, Ernst B. Hunziker, and Marcy Wong. Tissue Engineering. Mar. 2004, 10(3-4): 515-522.*
Hidenori Otsuka, et al.; "Characterization of Aldehyde-PEG Tethered Surfaces: Influence of PEG Chain Length on the Specific Biorecognition"; The ACS Journal of Surfaces and Colloids; Dec. 21, 2004; vol. 20 No. 26; pp. 11285-11287.
Marion Anhorn, et al.; "Specific Targeting of HER2 Overexpressing Brest Cancer Cells with Doxorubicin-Loaded Trastuzumab-Modified Human Serum Albumin Nanoparticles"; ACS Bioconjugate Chem., 2008, vol. 19; pp. 2321-2331.
Sun Hwa Kim, et al.; "LHRH Receptor-Mediated Delivery of siRNA Using Polyelectrolyte Complex Micelles Self-Assembled from si RNA-PEG-LHRH Conjugate and PEI"; ACS Bioconjugate Chem; 2008; vol. 19; pp. 2156-2162.

(Continued)

*Primary Examiner* — Alicia L Otton
(74) *Attorney, Agent, or Firm* — Sughrue Mion, PLLC

(57) ABSTRACT

A branched hetero polyethylene glycol according to the present invention is represented by the formula [1]:

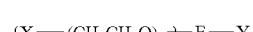

[1]

wherein X and Y represent each an atomic group containing at least a functional group which reacts with a functional group present in a bio-functional molecule to form a covalent bond and the functional group contained in the atomic group X and the functional group contained in the atomic group Y are different from each other; s is an integer of 2 to 8, which represents the number of polyethylene glycol chains; n is the number of average added moles for the polyethylene glycol chain and 20≤n≤2000; and E is a branching linker moiety having s-valent bonding valency for the polyethylene glycol chains and having monovalent bonding valency for the functional group Y.

3 Claims, No Drawings

(56) References Cited

OTHER PUBLICATIONS

Hongwei Zhang, et al.; "Efficient Transfection of Blood-Brain Barrier Endothelial Cells by Lipoplexes and Polyplexes in the Presence of Nuclear Targeting NLS-PEG-Acridine Conjugates"; ACS Bioconjugate Chem.; 2009; vol. 20; pp. 120-128.
Yanyan Jiang, et al.; "Active Tumor-targeted delivery of PEG-protein via transferrin-transferrin-receptor system"; Journal of Drug Targeting; Dec. 2007; vol. 15 No. 10; pp. 672-683.
International Search Report dated Aug. 16, 2011 issued in International Application No. PCT/JP2011/064154.
Office Action dated Jun. 30, 2014, issued by the State Intellectual Property Office of the People's Republic of China in counterpart Chinese Application No. 201180031483.6.
Communication dated Sep. 16, 2016 issued by the European Patent Office in counterpart European Patent Application No. 11798136.5.
Communication dated Sep. 6, 2016 issued by the Canadian Intellectual Property Office in counterpart Canadian Patent Application No. 2,803,556.
Office Action dated Nov. 29, 2016 issued by the Korean Intellectual Property Office in counterpart Korean Patent Application No. 10-2012-7033512.
Office Action dated May 4, 2018 by the Intellectual Property Office of India in counterpart Indian Patent Application No. 10743/CHENP/12.
Communication dated May 23, 2018 issued by the European Patent Office in counterpart European Patent Application No. 11798136.5.

* cited by examiner

BRANCHED HETERO POLYETHYLENE GLYCOL AND INTERMEDIATE

TECHNICAL FIELD

The present invention relates to a branched hetero polyethylene glycol. More specifically, the invention relates to a branched hetero polyethylene glycol compound which is used for modification of bio-functional molecules, drugs or drug carriers in drug delivery systems, materials and devices for diagnosis, or the like.

BACKGROUND ART

A polyethylene glycol itself exhibits low toxicity and antigenicity and has excellent solubility toward water and many organic solvents. Therefore, end-activated polyethylene glycol compounds where a reactive functional group is introduced into an end thereof have been widely used for imparting various functions, for example, imparting stealthiness of drugs and drug carriers in the body and solubilizing them in drug delivery systems, and improving bio-compatibility of material surfaces. Of the compounds, a so-called hetero bifunctional polyethylene glycol having functional groups different in reactivity at two ends of a linear polyethylene glycol, respectively, can introduce different molecules, for example, bio-functional molecules such as drugs, physiologically active substances, targeting substances, and the like into respective ends. Accordingly, the polyethylene glycol is used as a hetero crosslinker which crosslinks these bio-functional molecules each other or the bio-functional molecules and various drug carriers or devices.

A first characteristic advantage obtained by using the hetero bifunctional polyethylene glycol as such a hetero crosslinker is (A) a fact that low antigenicity and excellent solubility, which are properties of a polyethylene glycol as described above, can be imparted to the bonded substance. Since a polyethylene glycol is a polymer having repeating units, it has considerable molecular weight and number of monomer units and the distance between the ends is long as compared with a usual low-molecular-weight hetero crosslinker. Therefore, the next advantage is (B) a fact that substances which are difficult to bond directly owing to steric hindrance or molecules or substances which may lose a function intrinsic to the molecules, such as pharmacological activity, by direct bonding, or substances having different natures, such as molecules or substances and various drug carriers or devices can be bonded each other.

In the field of DDS, there are many studies on conjugates using the hetero bifunctional polyethylene glycol.

Jiang et al. (Non-Patent Document 1) have bonded transferrin to β-lactoglobulin using a hetero bifunctional polyethylene glycol having an N-hydroxysuccinimidoester group and a maleimide group. Zhang et al. (Non-Patent Document 2) have bonded NLS (nuclear localization signal) that is a peptide decamer to a dendrimer bonded substance of acridine using a hetero bifunctional polyethylene glycol having an N-hydroxysuccinimidoester group and a maleimide group. Kim et al. (Non-Patent Document 3) have bonded siRNA to LHRH (luteinizing hormone releasing hormone) using a hetero bifunctional polyethylene glycol having an amino group or a 2-pyridyldisulfide group and a carboxylic acid. Anhorn et al. (Non-Patent Document 4) have bonded an IgG antibody to a nanoparticle including an anticancer agent using a hetero bifunctional polyethylene glycol having an N-hydroxysuccinimidoester group and a maleimide group.

Moreover, as an application to diagnostic devices, Otsuka et al. (Non-Patent Document 5) have showed utilization as a biosensor which monitors a bio-functional molecule such as lectin, where lactose is bonded to polylactic acid using a hetero bifunctional polyethylene glycol having an acetal group and a hydroxyl group and, further utilizing interaction between lactose and lectin and interaction between polylactic acid and an inorganic substance surface, as a result, lectin and the inorganic substance surface is crosslinked.

As above, a hetero bifunctional polyethylene glycol is a hetero crosslinker widely used in medicament-related uses such as modification of bio-functional molecules, especially in DDS filed. On the other hand, when it is considered to enhance the function of the polyethylene glycol bonded substance where the hetero bifunctional polyethylene glycol is reacted with various bio-functional molecules, carriers, and the like, there is a case where plural modification of either one bio-functional molecule is desired. For example, in the case where a polyethylene glycol bonded substance having a drug at one end and a targeting molecule at another end bonded thereto is considered, when plural bonding of the drug is achieved, it becomes possible to improve transport efficiency. Moreover, when plural bonding of the targeting molecule is achieved, it becomes possible to improve targeting performance toward a ligand.

As a polyethylene glycol compound taking such plural modification of the bio-functional molecule into consideration, there is a description of so-called Forked-PEG in U.S. Pat. No. 6,362,254 (Patent Document 1).

In the patent, though there is no application example to hetero polyethylene glycol derivatives, Forked-PEG where two functional groups are introduced into one polyethylene glycol end has been synthesized for creating a branching point at one end of a methoxy-polyethylene glycol and for modifying a bio-functional molecule.

BACKGROUND ART DOCUMENTS

Patent Document

[Patent Document 1] U.S. Pat. No. 6,362,254

Non-Patent Documents

[Non-Patent Document 1] Journal of Drug Targeting, 2007, 15(10), 672-683
[Non-Patent Document 2] Bioconjugate Chem., 2009, 20, 120-128
[Non-Patent Document 3] Bioconjugate Chem., 2008, 19, 2156-2162
[Non-Patent Document 4] Bioconjugate Chem., 2008, 19, 2321-2331
[Non-Patent Document 5] Langmuir, 2004, 20(26), 11285-11287

DISCLOSURE OF THE INVENTION

Problems that the Invention is to Solve

However, in Patent Document 1, the length between the branching point and plurality of functional groups is not definitely defined and described examples are limited to those having a very near distance between two functional groups. When introduction of identical bio-functional molecules, especially substances having a very large molecular weight, such as proteins or antibodies, into the two functional groups are supposed, this means that an advantage that "(B) molecules which are difficult to bond directly owing to steric hindrance or molecules which may lose a function intrinsic to the molecules, such as pharmacological activity, by direct bonding can be bonded each other", which is a remarkable characteristic of the hetero polyethylene glycol derivative, is impaired to a large extent. Therefore, as an application to a hetero polyethylene glycol bonded substance having two or more identical bio-functional molecules and having one bio-functional molecule different from the above molecules at another end, which is a main purpose, utilization is limited.

Moreover, in the case where the introduction of two or more identical bio-functional molecules into a hetero polyethylene glycol derivative is supposed, a point largely different from the introduction of the bio-functional molecule into a usual monofunctional activated polyethylene glycol or hetero bifunctional polyethylene glycol is a fact that it is impossible to use an excess amount of the polyethylene glycol derivative relative to the bifunctional molecule for introducing the bio-functional molecule into two identical functional groups in high conversion since many kinds of impurity species are formed and rather the expensive bio-functional molecule should be allowed to react in an excess amount. Accordingly, also in view of cost, it is difficult to apply a structure having a short length between the branching point and plurality of functional groups.

From the above, in view of both performance and cost, in order to modify such a novel hetero polyethylene glycol derivative with bio-functional molecules, it is revealed that a hetero bifunctional polyethylene glycol having a sufficient distance not only between different functional groups but also between identical functional groups.

However, there has been no report of a hetero polyethylene glycol derivative having one of the two functional groups plurally, which is devised presupposing its use in medicament-related uses such as modification of such bio-functional molecules. Particularly, there is hitherto no example regarding the derivative designed also for the purpose of modifying bio-functional molecules having relatively large molecular weight, such as protein drugs and antibodies.

An object of the invention is to provide a branched hetero polyethylene glycol compound having two kinds of functional groups capable of reacting with various bio-functional molecules and having one of the functional groups plurally.

As such bio-functional molecules, there may be mentioned bio-functional molecules such as protein drugs, polypeptides, enzymes, antibodies, antibody medicaments, genes, nucleic acid compounds including oligonucleotides and the like, nucleic acid medicaments, anticancer agents, and low-molecular-weight drugs, as main ones. Also, other than these bio-functional molecules, carriers in drug delivery systems, such as liposomes and polymer micelles, and other materials and devices for diagnosis can be allowed to react. Of these, there is particularly provided a branched hetero polyethylene glycol compound most suitable for modifying bio-functional molecules including protein drugs, polypeptides, enzymes, antibodies, antibody medicaments, and the like.

Means for Solving the Problems

As a result of extensive studies for solving the above problems, the present inventors have developed a branched hetero polyethylene glycol compound having plurally one functional group of two kinds of functional groups, suitable for use in medicament-related uses including bio-functional molecules, drug carriers, and substance surfaces of base materials for diagnosis, particularly modification of bio-functional molecules having large molecular weight, including protein drugs, polypeptides, enzymes, antibodies, and antibody medicaments.

The most remarkable characteristic of the invention is a fact that plurally existing one functional group of the two kinds of the functional groups is present at an end of each polyethylene glycol chain having a certain range of the number of repeating units. Owing to this characteristic, in the case where it is considered to modify the branched hetero polyethylene glycol compound with two different kinds of bio-functional molecules, the bio-functional molecules bonded to the plural functional groups have a distance of two chains of the polyethylene glycol chain at most from each other and thus modification is achieved under the circumstances where mutual steric hindrance is reduced. Moreover, owing to the complexity of the molecular structure, the bio-functional molecules have a distance of one chain of the polyethylene glycol chain at most from the branching point which may reduce the reactivity due to steric hindrance and from another kind of bio-functional molecule to be modified at another kind of functional group.

As above, in the case where it is considered to modify the two different bio-functional molecules, owing to the structural characteristic of the branched hetero polyethylene glycol compound of the invention, the bio-functional molecule to be modified at the plurally existing one kind of functional group keeps a sufficient distance from any of three items, i.e., (1) the identical bio-functional molecule(s), (2) the branching point, and (3) the other kind of bio-functional molecule present in the same molecule. Therefore, it is possible to perform modification in higher efficiency with suppressing adverse effects resulting from steric hindrance and also a decrease in physiological activity can be suppressed.

Namely, the invention lies on the following.
(1) A branched hetero polyethylene glycol represented by the formula [1]:

[1]

(X and Y represent each an atomic group containing at least a functional group which reacts with a functional group present in a bio-functional molecule to form a covalent bond and the functional group contained in the atomic group X and the functional group contained in the atomic group Y are different from each other;

s is an integer of 2 to 8, which represents the number of polyethylene glycol chains;

n is the number of average added moles for the polyethylene glycol chain and 20≤n≤2000; and E is a branching linker moiety having s-valent bonding valency for the polyethylene glycol chains and having monovalent bonding valency for the functional group Y.)
(2) The branched hetero polyethylene glycol, wherein the branching linker moiety E is represented by the formula [2]:

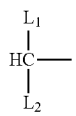
[2]

(CH is bonded to the functional group Y; L1 is a bonding moiety which bonds to p chain (s) of the polyethylene glycol chain, L2 is a bonding moiety which bonds to q chain (s) of the polyethylene glycol chain, and they are the same or different from each other; each of them is an ether bond, an ester bond, a urethane bond, an amide bond, a carbonate bond, a secondary amino group or a saturated hydrocarbon group containing the same, a single bond, or a saturated hydrocarbon group; and P and q are each an integer of 1 to 7 and p≥q and p+q=s.)
(3) The branched hetero polyethylene glycol, wherein L1 and L2 are each an ether bond, a urethane bond, an amide bond or a saturated hydrocarbon group containing the same, a single bond, or a saturated hydrocarbon group.
(4) The branched hetero polyethylene glycol, wherein L1 and L2 are both a saturated hydrocarbon group containing an ether bond, a single bond, or a saturated hydrocarbon group.
(5) The branched hetero polyethylene glycol, which is represented by the formula [3] or [4]:

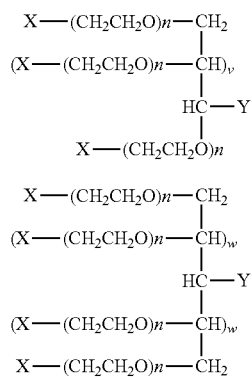

(v=0 or 2 and w=0 or 1.)
(6) The branched hetero polyethylene glycol, wherein the functional group of the atomic group X and the functional group of the atomic group Y are each selected from the group consisting of an acetal group, an aldehyde group, a maleimide group, a vinylsulfone group, an iodoacetamide group, an active ester group, an active carbonate group, a carboxyl group, an amino group, an aminoxy group, a thiol group, an allyl group, a vinyl group, an acetylene group, and an azide group.
(7) The branched hetero polyethylene glycol, wherein at least one of the functional group of the atomic group X and the functional group of the atomic group Y is selected from the group consisting of a carboxyl group, an amino group, an aminoxy group, and a thiol group.
(8) An intermediate, which is an intermediate of the branched hetero polyethylene glycol and wherein at least one of the functional group of the atomic group X and the functional group of the atomic group Y is protected by a protecting group.
(9) A polyethylene glycol bonded substance, wherein a bio-functional molecule is bonded to an end of the branched hetero polyethylene glycol.

Advantage of the Invention

The present invention provides a branched hetero polyethylene glycol compound having one functional group of two kinds of functional groups plurally, for use in chemical modification of protein drugs, polypeptides, enzymes, antibodies, antibody medicaments, genes, nucleic acid compounds including oligonucleotides, nucleic acid medicaments, anticancer agents, other drugs such as low-molecular-weight drugs, as main one and, in addition, functionalization of drug carriers in drug delivery systems, such as liposomes and polymer micelles, and other materials and devices for diagnosis. By using the branched hetero polyethylene glycol compound, it is possible to synthesize a polyethylene glycol bonded substance having plurally one of two kinds of bio-functional molecules effectively in a state that reaction inhibition by steric repulsion at modification and reduction of functions intrinsic to the molecule, such as physiological activity after modification are suppressed.

MODE FOR CARRYING OUT THE INVENTION

The hetero bifunctional polyethylene glycol is an end-activated polyethylene glycol compound having functional groups showing reactivity different in each of both ends of a linear polyethylene glycol chain, and different bio-functional molecules, surfaces, or the like can be introduced into the both ends.

The branched hetero polyethylene glycol in the invention has two kinds of functional groups at the ends similarly to the hetero bifunctional polyethylene glycol and the introduction of a different bio-functional molecule into each of the ends is a main purpose. Of the two kinds of functional groups, one kind thereof is plurally present and one of the bio-functional molecules to be introduced can be plurally modified. The branched hetero polyethylene glycol is represented by the formula [1].

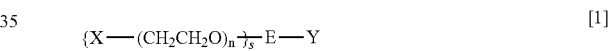

The polyethylene glycol chain represented by $(CH_2CH_2O)$ n is a linear polymer moiety having the number n of the repeating units separately defined as follows.

The atomic group X is an atomic group which is positioned at each polyethylene glycol chain end of the branched hetero polyethylene glycol represented by the formula [1] and may contain a bonding moiety. The atomic group X is represented by the formula [5] with the functional group X' and the bonding moiety W to be bonded to the functional group X'. However, the bonding moiety W may be a single bond. In this case, the atomic group X is coincident with the functional group X'.

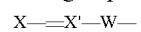                    [5]

The bonding moiety W is a linker having a function of bonding to the polyethylene glycol chain, and is not particularly limited so long as it is a moiety comprising a covalent bond. Preferably, there may be mentioned an ester bond, a urethane bond, an amide bond, an ether bond, a carbonate bond, a saturated hydrocarbon group containing a secondary amino group, a single bond, or a saturated hydrocarbon group. The saturated hydrocarbon group has 12 or less carbon atoms and, as preferred saturated hydrocarbon groups, a methylene group, an ethylene group, a trimethylene group, a propylene group, an isopropylene group, a tetramethylene group, a butylene group, an isobutylene group, a pentamethylene group, a hexamethylene group, and the like may be mentioned.

The functional group X' is not particularly limited so long as it is a functional group which reacts with functional groups present in bio-functional molecules including protein drugs, polypeptides, enzymes, antibodies, antibody medicaments, genes, nucleic acid compounds including oligonucleotides, nucleic acid medicaments, anticancer agents, and the other drugs such as low-molecular-weight drugs, which are objective substances for modification, to form a covalent bond. In an embodiment, X' is preferably a functional group capable of reacting with an amino group, a thiol group, an aldehyde group, a carboxyl group present in natural bio-functional molecules represented by proteins, or a maleimide group, a ketone group, an azide group, an acetylene group, or the like, which can be artificially introduced, under mild conditions in high yields, specifically, a group selected from the group consisting of an acetal group, an aldehyde group, a maleimide group, a vinylsulfone group, an iodoacetamide group, an active ester group, an active carbonate group, a carboxyl group, an amino group, an aminoxy group, a thiol group, an allyl group, a vinyl group, an acetylene group, and an azide group. Furthermore, in consideration of reaction efficiency, X' is more preferably a group selected from the group consisting of an acetal group, an aldehyde group, a maleimide group, an active ester group, an active carbonate group, an amino group, an aminoxy group, an acetylene group, and an azide group. An acetal group, an aldehyde group, an active carboxylic acid, an active carbonate group, or a carboxyl group is preferred in the case of reacting with an amino group of a bio-functional molecule to be an objective substance, a maleimide group, a vinylsulfone group, an iodoacetamide group, an allyl group, or a vinyl group is preferred in the case of reacting with a thiol group of a bio-functional molecule to be an objective substance, an amino group or an aminoxy group is preferred in the case of reacting with an aldehyde group or a ketone group of a bio-functional molecule to be an objective substance, an amino group, an aminoxy group, or a thiol group is preferred in the case of reacting with a carboxyl group of a bio-functional molecule to be an objective substance, a thiol group is preferred in the case of reacting with a maleimide group of a bio-functional molecule to be an objective substance, an acetylene group is preferred in the case of reacting with an azide group of a bio-functional molecule to be an objective substance, and an azide group is preferred in the case of reacting with an acetylene group of a bio-functional molecule to be an objective substance.

The atomic group Y is an atomic group which may contain a bonding moiety to be bonded to a branching bonding moiety E, and is represented as the formula [6] with a functional group Y' and a bonding moiety W' which may be contained in the atomic group Y. Incidentally, the bonding moiety W' may be a single bond. In this case, the atomic group Y is coincident with the functional group Y'.

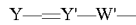

[6]

The bonding moiety W' has the same definition as the bonding moiety W which may be contained in the above X. The functional group Y' is not particularly limited so long as it is a functional group which reacts with functional groups present in bio-functional molecules including protein drugs, polypeptides, enzymes, antibodies, antibody medicaments, genes, nucleic acid compounds including oligonucleotides, nucleic acid medicaments, anticancer agents, and the other drugs such as low-molecular-weight drugs, which are objective substances for modification, to form a covalent bond. In a preferred embodiment, Y' is preferably a functional group capable of reacting with an amino group, a thiol group, an aldehyde group, a carboxyl group present in natural bio-functional molecules represented by proteins, or a maleimide group, a ketone group, an azide group, an acetylene group, or the like, which can be artificially introduced, under mild conditions in high yields, specifically, a group selected from the group consisting of an acetal group, an aldehyde group, a maleimide group, a vinylsulfone group, an iodoacetamide group, an active ester group, an active carbonate group, a carboxyl group, an amino group, an aminoxy group, a thiol group, an allyl group, a vinyl group, an acetylene group, and an azide group. Furthermore, in consideration of reaction efficiency, Y' is more preferably a group selected from the group consisting of an acetal group, an aldehyde group, a maleimide group, an active ester group, an active carbonate group, an amino group, an aminoxy group, an acetylene group, and an azide group.

The acetal group in the invention inclusive of the bonding moiety is represented by the formula [7], wherein R is a saturated hydrocarbon group having 8 or less carbon atoms. R is preferably a saturated hydrocarbon group having 4 or less carbon atoms, most preferably an ethyl group. In general, the acetal group having such a structure is a protecting group of an aldehyde group but, since deprotection of the acetal group can be conveniently performed with weak acidity, the nature at the use in the reaction with the bio-functional molecule is very close to that of the other functional groups and thus it is possible to handle the group almost similarly. Accordingly, in the invention, the acetal group is defined as a functional group having an electrophilic reactivity similarly to aldehyde.

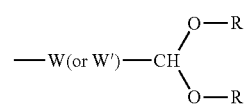

[7]

The maleimide group in the invention inclusive of the bonding moiety is a group represented by the formula [8] and is reactive with nucleophilic groups such as a thiol group. R1 is preferably hydrogen or a methyl group, more preferably hydrogen.

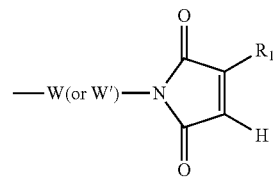

[8]

The active ester group in the invention inclusive of the bonding moiety is a group represented by the formula [9] and is reactive with nucleophilic groups such as an amino group. R2 is preferably a phenyl group, a 3-pyridyl group, a succinimide group, a 2-benzothiazole group, or a 1-benzotriazole group, more preferably a succinimide group or a 1-benzotriazole group, and most preferably a succinimide group.

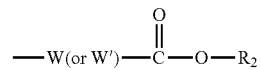

[9]

The active carbonate group in the invention inclusive of the bonding moiety is a group represented by the formula [10] and is reactive with nucleophilic groups such as an amino group. R3 is preferably a 4-nitrophenyl group, a succinimide group, or a 1-benzotriazole group, more preferably a 4-nitrophenyl group or a succinimide group, and most preferably a succinimide group.

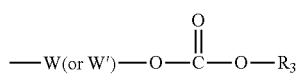

[10]

The acetylene group in the invention inclusive of the bonding moiety is a group represented by the formula [11] and is reactive with an azide group and the like. R4 is preferably a saturated hydrocarbon group having 8 or less carbon atoms or hydrogen, more preferably hydrogen.

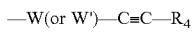

[11]

The functional group contained in the atomic group X and the functional group contained in the atomic group Y should be different from each other. However, the bonding moiety W contained in the atomic group X and the bonding moiety W' contained in the atomic group Y may be the same or different from each other.

As combination of the functional group X' and the functional group Y', Y' is a group selected from a maleimide group, a vinylsulfone group, an iodoacetamide group, an active ester group, an active carbonate group, an amino group, and an aminoxy group when X' is an acetal group, Y' is a group selected from a maleimide group, a vinylsulfone group, an acetylene group, and an azide group when X' is an aldehyde group, Y' is a group selected from an acetal group, an active ester group, an active carbonate group, an acetylene group, and an azide group when X' is a maleimide group, a vinylsulfone group, or an iodoacetamide group, Y' is a group selected from an acetal group, a maleimide group, a vinylsulfone group, an iodoacetamide group, an acetylene group, and an azide group when X' is an active ester group or an active carbonate group, Y' is a group selected from an acetal group, an acetylene group, and an azide group when X' is an amino group or an aminoxy group, Y' is a group selected from an acetal group, an aldehyde group, a maleimide group, a vinylsulfone group, an iodoacetamide group, an active ester group, an active carbonate group, an amino group, and an aminoxy group when X' is an acetylene group or an azide group. Most preferably, Y' is a group selected from a maleimide group, an active ester group, an active carbonate group, an amino group, and an aminoxy group when X' is an acetal group, Y' is a group selected from an acetal group, an active ester group, an active carbonate group, an acetylene group, and an azide group when X' is a maleimide group, Y' is a group selected from an acetal group, a maleimide group, an acetylene group, and an azide group when X' is an active ester group or an active carbonate group, Y' is a group selected from an acetal group, an acetylene group, and an azide group when X' is an amino group or an aminoxy group, Y' is a group selected from an acetal group, a maleimide group, an active ester group, an active carbonate group, an amino group, and an aminoxy group when X' is an acetylene group or an azide group.

In the invention, in view of the reactivity, stability, and the like, at least one of the functional group of the atomic group X and the functional group of the atomic group Y is preferably selected from the group consisting of a carboxyl group an amino group, an aminoxy group, and a thiol group.

E is a branching linker moiety having s-valent bond for the polyethylene glycol chain having the atomic group X at an end and monovalent bond for the atomic group Y, and E is not particularly limited so long as it is a covalent bond but preferably has a structure represented by the formula [2].

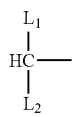

[2]

In the formula, CH (methine group) is directly bonded to the atomic group Y. L1 and L2 are bonding moieties which bond to p chain(s) and q chain(s) of the above polyethylene glycol chain {X—(CH$_2$CH$_2$O)n-}, respectively. They may be the same or different from each other and are selected from an ether bond, an ester bond, a urethane bond, an amide bond, a carbonate bond or a secondary amino group or a saturated hydrocarbon group containing the same, a single bond, or a saturated hydrocarbon group. L1 and L2 are each preferably an ether bond, a urethane bond, an amide bond, or a saturated hydrocarbon group containing the same, a single bond, or a saturated hydrocarbon group, more preferably a saturated hydrocarbon group containing an ether bond, a saturated hydrocarbon group, or a single bond, and most preferably a saturated hydrocarbon group or a single bond. P and q represent each the number of the polyethylene glycol chain {X—(CH$_2$CH$_2$O)n-} to be bonded to L1 and L2, respectively. p and q are each an integer of 1 to 7 where p≥q and have a relation of p+q=s. Preferably, p=q=1 or p=3, q=1 or p=q=2, and most preferably p=q=1. More specifically, E is preferably represented by the formula [12] or the formula [13], where v is 0 or an integer of 1 to 6 and w is 0 or an integer of 1 to 3. Preferably, v and w are as follows: v=0 or 2; w=0 or 1, respectively.

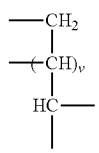

[12]

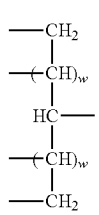

[13]

The branched hetero polyethylene glycol of the invention where the above E is represented by the formula [12] or the formula [13] is represented by the formula [3] or the formula [4], respectively.

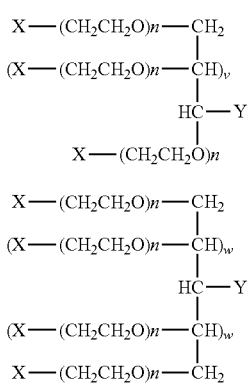

[3]

[4]

s is an integer indicating the number of polymers of the polyethylene glycol chain to be bonded to the atomic group X at one end and to the branching linker moiety E at another end and is 2 to 8, preferably 2 or 4.

n is the number of the repeating units per the polyethylene glycol chain having the atomic group X at the end and, in the invention, it is defined to be one calculated by various theoretical calculations based on the number-average molecular weight (Mn) of the compound. Regarding n, the most suitable setting is necessary for efficiently modifying the bio-functional molecules and thoroughly exhibiting the function. Specifically, in the case where a bio-functional molecule including a protein drug, an antibody, or the like is modified at the atomic group X and the other bio-functional molecule, surface, or the like is modified at the atomic group Y, it is necessary to keep a sufficient distance as to any of three relationships, i.e., (1) each of plural identical bio-functional molecules which are modified at the atomic group X, (2) the bio-functional molecules which are modified at the atomic group X and the branching point, and (3) the bio-functional molecules which are modified at the atomic group X and the bio-functional molecule or surface which is modified at the atomic group Y. From this viewpoint, the lower limit of n is preferably 20, more preferably 50, further preferably 80, and most preferably 120. Also, owing to difficulty in operation by an increase in solution viscosity and increase in molecular weight distribution by heterogeneity of an ethylene oxide addition reaction, the molecular weight in the branched hetero polyethylene glycol to be used in the present use should be suppressed to a certain value or less. From this viewpoint, the upper limit of n is preferably 2,000, more preferably 1,500, further preferably 1,000, and most preferably 500. By such selection of an appropriate range of n, it is possible to synthesize and use the bonded substance in a state that reaction inhibition to be induced by steric repulsion between plurality of the bio-functional molecules which are modified at the functional groups X and Y, influence of the sterically crowded branching linker moiety E, and reduction of the functions intrinsic to the molecules, such as pharmacological activity after modification, are suppressed and further adverse effects on the reaction or the operability and quality to be induced by a viscosity increase in the use of the bonded substance and an increase of molecular weight distribution are also suppressed.

With regard to the branched hetero polyethylene glycol of the invention, as a process for introducing the polyethylene glycol chain, a coupling reaction of polyethylene glycol chains or a polymerization reaction of ethylene oxide can be selected.

As the introduction of the polyethylene glycol chain by the coupling reaction, a procedure of reacting a substrate having two amino groups such as lysine with a methoxy-polyethylene glycol having, for example, an active carbonate group at the end, which is reactive to the amino group, may be mentioned as a typical example In order to synthesize the branched hetero polyethylene glycol of the invention, it is necessary to use not a methoxy-polyethylene glycol derivative but a hetero bifunctional polyethylene glycol as a polyethylene glycol. Thereafter, if necessary, a remaining end group of the two chains of the hetero bifunctional polyethylene glycol introduced and the carboxylic acid of lysine are subjected to functional group conversion. As the reaction for use in the functional group conversion, any hitherto known methods can be used but conditions not decomposing the bond formed by the coupling reaction should be appropriately selected. The bond formed by the coupling is determined by the combination of the functional groups to be used in the reaction and, in this case, is an ester bond, a urethane bond, an amide bond, a carbonate bond, a secondary amino group, or the like.

As a typical example of introducing the polyethylene glycol chain by the polymerization of ethylene oxide and subsequently introducing functional groups into the ends, the following steps may be mentioned.

(A) Polymerization of Ethylene Oxide

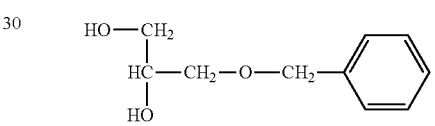

[14]

Ethylene oxide is polymerized to the remaining two hydroxyl groups of the compound of the formula [14] where the hydroxyl group at 3-position of glycerin has been substituted with a benzyl group, in an amount of 40 to 4,000 molar equivalents to the compound of the formula [14] in toluene or without any solvent under an alkali condition of metal sodium or metal potassium, sodium hydride, potassium hydride, sodium methoxide, potassium t-butoxide, or the like to obtain a branched hetero polyethylene glycol of the formula [15].

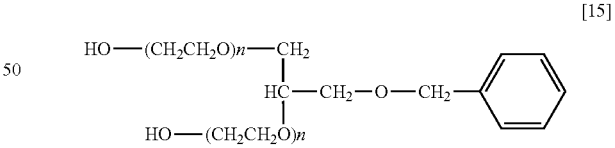

[15]

In the formula, the branching moiety corresponding to E of the formula [1] is the same as one defined in the formula [2]. The branching moiety to be used in the polymerization step of ethylene oxide is preferably a stable group under such an alkali condition, more preferably a saturated hydrocarbon group or a saturated hydrocarbon group containing an ether bond. As the skeleton of the branching moiety, most preferably, a glycerin moiety, a xylitol moiety, and the like may be mentioned. Moreover, instead of a benzyl group, the other protecting group can be used so long as it is a stable group under the above alkali condition. For example, there may be used a tetrahydropyranyl group, a t-butyl group, and the like in the case of a protecting group for a hydroxyl group and an acetal group such as a diethyl acetal group in the case of a protecting group for an aldehyde group.

(B) Functional Group Conversion of Hydroxyl Group at Polyethylene Glycol Chain End Subsequently, after toluene is added to the branched polyethylene glycol compound of the formula [15] and is refluxed under ordinary pressure to achieve removal of water, an excess amount of methanesulfonyl chloride is added in the presence of a base such as triethylamine to form a mesylate. This compound is allowed to react with a sodium alcoholate compound of 3,3-diethoxy-1-propanol to introduce a diethoxy acetal group, thereby a compound of the formula [16] being obtained.

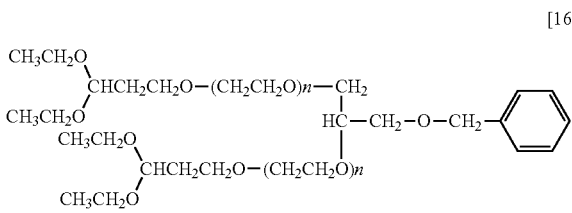

[16]

Other than the acetal group, it is possible to introduce various protecting groups and functional groups into ends of polyethylene glycol chains. However, in the formula [16], a point to be noted is a fact that it is necessary to perform functional group conversion of the hydroxyl group under conditions where the protecting group in the vicinity of the branching moiety that is a benzyl group in this case can be stably present. For example, it is necessary that such a reaction condition that it does not become reductive one is selected in the case of using a benzyl group as a protecting group, and such a reaction condition that it does not become acidic one is selected in the case of using a tetrahydropyranyl group, a diethyl acetal group, or the like.

(C) Deprotection of Protecting Group in Vicinity of Branching Moiety

Next, catalytic reduction of the compound of the formula [16] is carried out in the presence of a reduction catalyst such as Pd/C and a hydrogen donor such as hydrogen gas or cyclohexene to achieve a debenzylation reaction, thereby a compound of the formula [17] being obtained.

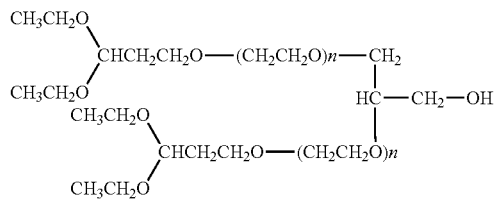

[17]

On this occasion, the functional group/protecting group introduced into the polyethylene glycol chain end should be a stable group under the deprotection condition for the deprotection of the protecting group in the vicinity of the branching moiety, as a result of the functional group conversion at one time or plurality of times as in the above step (B).

For example, as a group to be introduced into the polyethylene glycol chain, it is necessary to select a stable protecting group/functional group against hydrogen reduction that is a deprotection condition, such as an acetal group, a tetrahydropyranyl group, a phthalimide group, an oxyphthalimide group, or a thiol group, in the case of using a benzyl group as a protecting group of the hydroxyl group in the vicinity of the branching moiety; a stable protecting group/functional group against a weakly acidic condition that is a deprotection condition, such as a maleimide group, a carboxyl group, an amino group, an aminoxy group, or a thiol group, in the case of using a tetrahydropyranyl group as a protecting group of the hydroxyl group or an acetal group or the like as a protecting group of an aldehyde group; a stable protecting group/functional group against a strongly acidic condition that is a deprotection condition, such as a carboxyl group, an amino group, an aminoxy group, or a thiol group, in the case of using a t-butoxy group or the like. However, since enormous numbers of reactions are present for the functional group conversion and subsequent further functional group conversion is possible, this description does not limit the finally obtained functional group species at the end.

Incidentally, in the case where an acetal group such as a diethyl acetal group that is a protecting group of an aldehyde is used as a protecting group in the vicinity of the branching moiety, since it is possible to use the group as it is for deprotection and reaction in the reaction system as mentioned above, it is not always necessary to perform deprotection at this stage.

(D) Functional Group Conversion in Vicinity of Branching Moiety

Next, the compound of the formula [17] is subjected to functional group conversion to introduce various functional groups as follows. After toluene is added and is refluxed under ordinary pressure to achieve removal of water, an excess amount of methanesulfonyl chloride is added in the presence of triethylamine to form a mesylate. Then, this compound is allowed to react with ammonia to introduce an amino group, thereby a compound of the formula [18] being obtained.

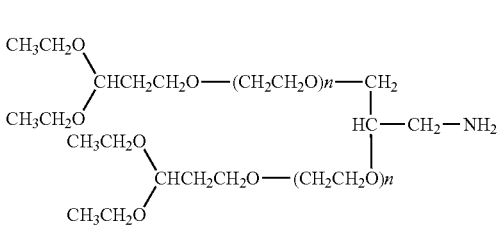

[18]

Further, the compound of the formula [18] is allowed to react with N-succinimidylmaleimidopropionic acid in the presence of a base such as N-methylmorpholine to introduce a maleimide group, thereby a compound of the formula [19] being obtained.

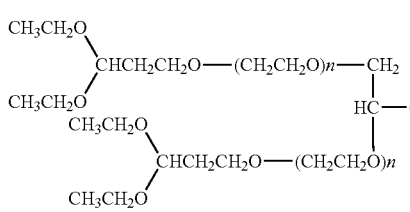 

[19]

The branched hetero polyethylene glycol having plurality of functional groups at polyethylene glycol chain ends and a functional group in the vicinity of the branching moiety introduced thereinto as the formulae [18] and [19] can be used for the reactions with bio-functional molecules.

(E) Functional Group Conversion/Deprotection at Polyethylene Glycol Chain Ends

The branched hetero polyethylene glycol represented by the formula [18] or [19] can be used for the reaction with bio-functional molecules in this state. However, for example, regarding the compound of the formula [19], by selecting an appropriate acidic condition, it is also possible to perform deprotection with leaving the maleimide group to convert the acetal group to an aldehyde group.

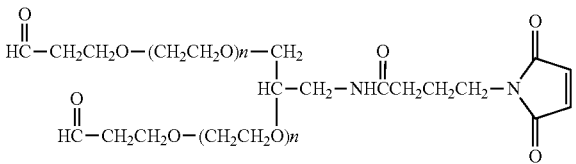

[20]

It is also possible to repeat the steps of functional group conversion such as the above (D) and (E) several times for the purpose of introduction of respective arbitrary functional groups and it is possible to introduce various kinds of functional groups by performing functional group conversion under aforementioned conditions.

The objective substances to be bonded to the branched hetero polyethylene glycol of the invention are bio-functional molecules including protein drugs, polypeptides, enzymes, antibodies, antibody medicaments, genes, nucleic acid compounds including oligonucleotides, nucleic acid medicaments, anticancer agents, the other drugs such as low-molecular-weight drugs or the other molecules, or carriers in drug delivery systems, such as liposomes and polymer micelles, and other materials and devices for diagnosis. As a typical example, there may be mentioned an example where a targeting molecule such as an antibody or a peptide ligand is introduced into the atomic group X and a drug such as an anticancer agent or a protein drug or a carrier containing a drug included therein, such as a liposome or a polymer micelle, is bonded to another atomic group Y. In this case, it is expected to remarkably enhance migration ability of the drug or carrier to an objective tissue as compared with the case of using a conventional hetero bifunctional polyethylene glycol where one targeting molecule is bonded. As another example, there may be mentioned an example where a drug is introduced into the atomic group X and a targeting molecule is introduced into another atomic group Y. In this case, a large amount of the drug can be introduced and thus it is expected to enhance the amount of the drug to be transported as compared with the case of using the hetero bifunctional polyethylene glycol. The bio-functional molecules to be reacted and introduced into the atomic group X and the atomic group Y are not particularly limited. However, when the number n of the repeating units per the polyethylene glycol chain having the atomic group X and the structural characteristic of the branched hetero polyethylene glycol of the invention are considered, a larger advantage can be obtained by using a bio-functional molecule having a molecular weight of 2,000 or more, further preferably 3,000 or more for the atomic group X. Also, there is no particular limitation but, form the same viewpoint, a larger advantage can be obtained by using a bio-functional molecule having a molecular weight of 3,000 or less, further preferably 2,000 or less for the atomic group Y.

EXAMPLES

The following will describe the invention in further detail with reference to Examples.

The molecular weight and molecular weight distribution of polyethylene glycol compounds including the branched hetero polyethylene glycol or intermediates thereof were determined by analysis on gel permeation chromatography (GPC). In the invention, measurement was performed using SHODEX GPC SYSTEM-11 as a GPC system and SHODEX RIX8 as a differential refractometer that was a detector, connecting three columns of SHODEX KF801L, KF803L, and KF804L (φ 8 nm×300 mm) serially, setting the temperature of the column oven to 40° C., using tetrahydrofuran as an eluent, setting the flow rate to 1 ml/minute, setting the concentration of a sample to 0.1% by mass, and setting an injection volume to 0.1 ml. As a calibration curve, a curve prepared using ethylene glycol, diethylene glycol, and triethylene glycol manufactured by Kanto Chemical Co., Inc. and Polymer Standards for GPC of polyethylene glycols or polyethylene oxides each having a molecular weight of 600 to 70,000 manufactured by Polymer Laboratory was used. For data analysis, BORWIN GPC calculation program was used. Mn indicates number-average molecular weight, Mw indicates weight-average molecular weight, and Mp indicates peak-top molecular weight. As for the molecular weight distribution, a calculated value thereof was shown as Mw/Mn.

For $^1$H-NMR analysis, JNM-ECP400 or JNM-ECA600 manufactured by JEOL DATUM Ltd. was used. Measurement was performed using CDCl$_3$ as a deuterated solvent, using a φ 5 mm tube, and using TMS as an internal standard substance.

Example 1

To a 300 ml four-neck flask equipped with a thermometer, a nitrogen-inlet tube, and a stirrer were added 18.2 g (0.1 mol) of 3-benzyloxy-1,2-propanediol, 150 g of anhydrous toluene, 0.9 g (39 mmol:26% by mol) of metal sodium, and the whole was stirred at room temperature with introducing nitrogen until metal sodium was dissolved. The solution was charged into a 5 L autoclave and, after inside of the system was replaced with nitrogen, the temperature was raised to 100° C. After 1,982 g (45 mol) of ethylene oxide was added thereto at 100 to 130° C. under a pressure of 1 MPa or less, the reaction was further continued for 2 hours. After unreacted ethylene oxide gas was removed under reduced pressure, the whole was cooled to 60° C. and pH was adjusted to 7.5 with an 85% aqueous phosphoric acid solution to obtain the following compound (a1).

$^1$H-NMR; δ (ppm):
3.40-3.90 (1785H, m, HO(CH$_2$CH$_2$O)$_n$—CH$_2$, HO(CH$_2$CH$_2$O)$_n$—CH, CH$_2$O—CH$_2$Ph), 4.54 (2H, s, —CH$_2$Ph), 7.27-7.38 (5H, m, —CH$_2$Ph)

GPC analysis;
number-average molecular weight (Mn): 19,654, weight-average molecular weight (Mw): 20,285, polydispersity (Mw/Mn): 1.032

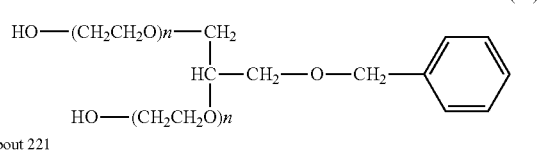

(a1)

n = about 221

Example 2

Into a 3 L four-neck flask fitted with a thermometer, a nitrogen-inlet tube, a stirrer, a Dean-stark tube, and a cooling tube were charged 372 g (18.6 mmol) of the above compound (a1) and 1,860 g of toluene. The whole was heated under reflux and water was removed as an azeotrope. After cooling to room temperature, 6.02 g (59.5 mmol) of triethylamine and 5.54 g (48.4 mmol) of methanesulfonyl chloride were added thereto and allowed to react at 40° C. for 3 hours. Subsequently, a toluene (256.8 g) solution of 85.6 g (465 mmol) of 3,3-diethoxy-1-propanol containing 2.58 g (112 mmol) of sodium dissolved therein was added thereto, followed by reaction at 70° C. for 5 hours. After filtration of the reaction solution, the filtrate was transferred to a 10 L stainless steel pot and crystallization was performed with adding 1.488 g of ethyl acetate, 1,488 g of ethanol, and 2,976 g of hexane. After the precipitated crystals were filtrated to remove the solvents, the crystals were transferred to a 10 L stainless steel pot. After 1,488 g of ethyl acetate and 1,488 g of ethanol were added thereto and heated to dissolve the crystals at 40° C., the solution was cooled to 20° C. and crystallization was performed with adding 2.976 g of hexane. Thereafter, similar crystallization was repeated three times and, after washing with hexane, the crystals were collected by filtration and dried to obtain the following compound (a2).

$^1$H-NMR; δ (ppm):
1.16-1.24 (12H, t, (CH$_3$CH$_2$O)$_2$—CHCH$_2$CH$_2$—), 1.85-1.95 (4H, q, (CH$_3$CH$_2$O)$_2$—CHCH$_2$CH$_2$—), 3.40-3.90 (1725H, m, —(CH$_2$CH$_2$O)$_n$—CH$_2$, —(CH$_2$CH$_2$O)$_n$—CH, CH$_2$O—CH$_2$Ph, (CH$_3$CH$_2$O)$_2$—CHCH$_2$CH$_2$—), 4.54 (2H, s, —CH$_2$Ph), 4.60-4.68 (2H, t, (CH$_3$CH$_2$O)$_2$—CHCH$_2$CH$_2$—), 7.27-7.38 (5H, m, —CH$_2$Ph)

GPC analysis;
number-average molecular weight (Mn): 19,190, weight-average molecular weight (Mw): 19,496, polydispersity (Mw/Mn): 1.016

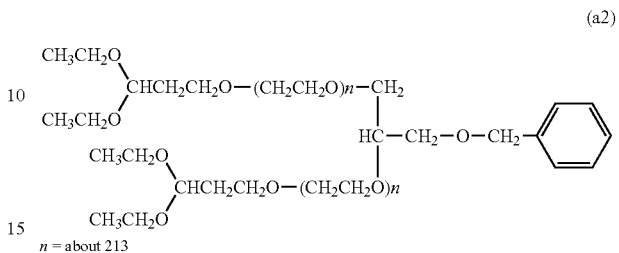

(a2)

n = about 213

Example 3

Into a 1 L four-neck flask fitted with a thermometer, a nitrogen-inlet tube, a stirrer, and a cooling tube were charged 50 g of the above compound (a2) and 25 g of 5% palladium-carbon (a 50% hydrous product). After replacement with nitrogen, 400 g of methanol and 67 g of cyclohexene were added thereto, the temperature was raised, and gentle refluxing was performed at 52 to 55° C. to effect reaction for 2 hours. After cooling of the reaction solution to room temperature, palladium-carbon was filtrated off and the filtrate was concentrated. To the concentrate were added 400 g of toluene and 200 g of hexane, and crystallization was performed. The resulting crystals were collected by filtration and dried to obtain the following compound (a3).

$^1$H-NMR; δ (ppm):
1.16-1.24 (12H, t, (CH$_3$CH$_2$O)$_2$—CHCH$_2$CH$_2$—), 1.85-1.95 (4H, q, (CH$_3$CH$_2$O)$_2$—CHCH$_2$CH$_2$—), 3.40-3.90 (1673H, m, —(CH$_2$CH$_2$O)$_n$—CH$_2$, —(CH$_2$CH$_2$O)$_n$—CH, CH$_2$OH, (CH$_3$CH$_2$O)$_2$—CHCH$_2$CH$_2$—), 4.60-4.68 (2H, t, (CH$_3$CH$_2$O)$_2$—CHCH$_2$CH$_2$—)

GPC analysis;
number-average molecular weight (Mn): 18,573, weight-average molecular weight (Mw): 19,123, polydispersity (Mw/Mn): 1.030

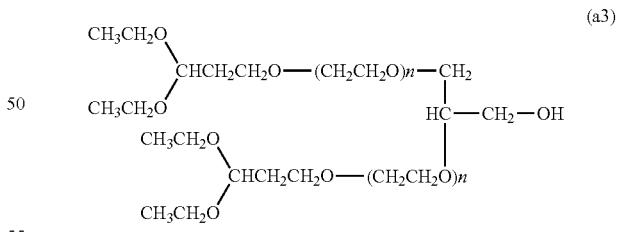

(a3)

n = about 207

Example 4

Into a 200 mL three-neck flask fitted with a thermometer, a nitrogen-inlet tube, a stirrer, a Dean-stark tube, and a cooling tube were charged 13.1 g (0.66 mmol) of the above compound (a3) and 79 g of toluene. The whole was heated under reflux and water was removed as an azeotrope. After cooling to room temperature, 0.33 g (3.3 mmol) of triethylamine and 0.30 g (2.6 mmol) of methanesulfonyl chloride were added thereto and allowed to react at 40° C. for 3 hours. After filtration of the reaction solution, the filtrate was transferred to a 300 mL beaker and crystallization was performed with adding 100 g of ethyl acetate and 50 g of hexane. After the precipitated crystals were filtrated to remove the solvents, the crystals were transferred to a 10 L stainless steel pot. After 1,488 g of ethyl acetate and 1,488 g of ethanol were added thereto and heated to dissolve the crystals at 40° C., the solution was cooled to 20° C. and crystallization was performed with adding 2,976 g of hexane. Thereafter, similar crystallization was repeated three times and, after washing with hexane, the crystals were collected by filtration and dried to obtain the following compound (a4).

$^1$H-NMR; δ (ppm):

1.16-1.24 (12H, t, (C$\underline{\text{H}}_3$CH$_2$O)$_2$—CHCH$_2$CH$_2$—), 1.85-1.95 (4H, q, (CH$_3$CH$_2$O)$_2$—CHC$\underline{\text{H}}_2$CH$_2$—), 3.08 (3H, s, —OSO$_2$C$\underline{\text{H}}_3$), 3.40-3.90 (1732H, m, —(C$\underline{\text{H}}_2$CH$_2$O)$_n$—C$\underline{\text{H}}_2$, —(CH$_2$C$\underline{\text{H}}_2$O)$_n$—C$\underline{\text{H}}$, C$\underline{\text{H}}_2$OH, (CH$_3$C$\underline{\text{H}}_2$O)$_2$—CHCH$_2$C$\underline{\text{H}}_2$—), 4.24-4.44 (2H, m, —C$\underline{\text{H}}_2$O—OSO$_2$CH$_3$), 4.60-4.68 (2H, t, (CH$_3$CH$_2$O)$_2$—C$\underline{\text{H}}$CH$_2$CH$_2$—)

GPC analysis;

number-average molecular weight (Mn): 19,274, weight-average molecular weight (Mw): 20,046, polydispersity (Mw/Mn): 1.040

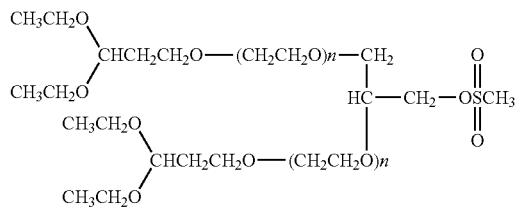

(a4)

$n$ = about 214

Example 5

Into a 100 mL three-neck flask fitted with a thermometer, a nitrogen-inlet tube, a stirrer, a Dean-stark tube, and a cooling tube were charged 10.0 g (0.50 mmol) of the above compound (a4), 80 g of ammonia water, and 20 g of ion-exchange water, followed by reaction at 55° C. for 8 hours. Ammonia was removed at 55° C. under slightly reduced pressure for 10 hours, followed by extraction with adding 100 g of chloroform. After the chloroform solution was concentrated, 52 g of toluene was added thereto and the concentrate was dissolved at 40° C., followed by filtration. Thereafter, crystallization was performed with adding 30 g of hexane at room temperature in a 200 mL beaker. After the precipitated crystals were filtrated to remove the solvents, the crystals were washed with hexane, collected by filtration, and dried to obtain the following compound (a5).

$^1$H-NMR; δ (ppm):

1.16-1.24 (12H, t, (C$\underline{\text{H}}_3$CH$_2$O)$_2$—CHCH$_2$CH$_2$—), 1.85-1.95 (4H, q, (CH$_3$CH$_2$O)$_2$—CHC$\underline{\text{H}}_2$CH$_2$—), 2.70-2.95 (2H, m, —C$\underline{\text{H}}_2$NH$_2$), 3.40-3.90 (1730H, m, —(C$\underline{\text{H}}_2$CH$_2$O)$_n$—C$\underline{\text{H}}_2$, —(CH$_2$C$\underline{\text{H}}_2$O)$_n$—C$\underline{\text{H}}$, C$\underline{\text{H}}_2$OH, (CH$_3$C$\underline{\text{H}}_2$O)$_2$—CHCH$_2$C$\underline{\text{H}}_2$—), 4.60-4.68 (2H, t, (CH$_3$CH$_2$O)$_2$—C$\underline{\text{H}}$CH$_2$CH$_2$—)

GPC analysis;

number-average molecular weight (Mn): 19,217, weight-average molecular weight (Mw): 20,362, polydispersity (Mw/Mn): 1.060

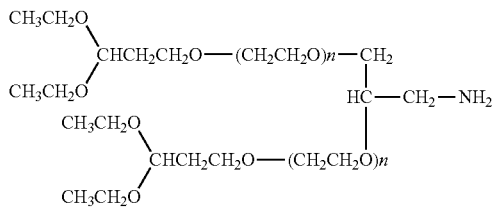

(a5)

$n$ = about 214

Example 6

Into a 100 mL three-neck flask fitted with a thermometer, a nitrogen-inlet tube, a stirrer, a Dean-stark tube, and a cooling tube were charged 5.0 g (0.25 mmol) of the above compound (a5), 26 g of toluene, 4.0 g of acetonitrile, N-methylmorpholine (1.25 mmol), and N-succinimidyl 3-maleimidopropionate (0.375 mmol), followed by reaction at room temperature for 4 hours. After the solution was filtrated, crystallization was performed with adding 100 g of ethyl acetate and 50 g of hexane at room temperature in a 300 mL beaker. Then, after 100 g of ethyl acetate was added and the crystals were dissolved at 40° C., the solution was cooled to room temperature and 100 g of hexane was added to precipitate crystals. After the crystallization was repeated further twice, the crystals were washed with hexane, collected by filtration, and dried to obtain the following compound (a6).

$^1$H-NMR; δ (ppm):

1.16-1.24 (12H, t, (C$\underline{\text{H}}_3$CH$_2$O)$_2$—CHCH$_2$CH$_2$—), 1.85-1.95 (4H, q, (CH$_3$CH$_2$O)$_2$—CHC$\underline{\text{H}}_2$CH$_2$—), 2.51 (2H, t, NHCOC$\underline{\text{H}}_2$CH$_2$), 3.40-3.90 (1736H, m, —(C$\underline{\text{H}}_2$CH$_2$O)$_n$—C$\underline{\text{H}}_2$, —(CH$_2$C$\underline{\text{H}}_2$O)$_n$—C$\underline{\text{H}}$, C$\underline{\text{H}}_2$OH, (CH$_3$C$\underline{\text{H}}_2$O)$_2$—CHCH$_2$C$\underline{\text{H}}_2$—, C$\underline{\text{H}}_2$NHCOC$\underline{\text{H}}_2$CH$_2$), 4.60-4.68 (2H, t, (CH$_3$CH$_2$O)$_2$—C$\underline{\text{H}}$CH$_2$CH$_2$—), 6.70 (2H, s, C$\underline{\text{H}}$=C$\underline{\text{H}}$)

GPC analysis;

number-average molecular weight (Mn): 19,395, weight-average molecular weight (Mw): 20,600, polydispersity (Mw/Mn): 1.062

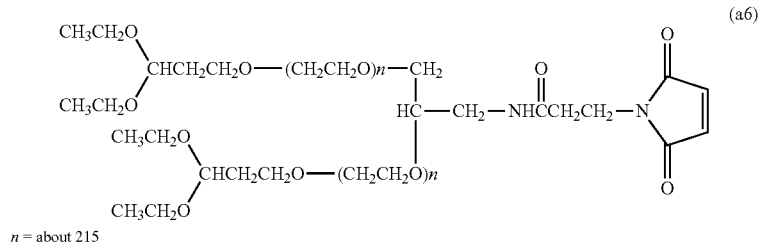

(a6)

$n$ = about 215

Example 7

Into a 200 mL beaker fitted with a thermometer, a nitrogen-inlet tube, and a stirring bar were charged 2.0 g (0.10 mmol) of the above compound (a5) and 40 g of ion-exchange water, followed by dissolution. After the solution was prepared to be pH 2 with hydrochloric acid and stirred at room temperature for 2 hours, the solution was neutralized to pH 6 with an aqueous sodium hydroxide solution, followed by extraction with adding 100 g of chloroform. After the chloroform solution was concentrated, 40 g of toluene was added thereto and the concentrate was dissolved at 40° C., followed by filtration. Thereafter, crystallization was performed with adding 20 g of hexane at room temperature in a 200 mL beaker. After the precipitated crystals were filtrated to remove the solvents, the crystals were washed with hexane, collected by filtration, and dried to obtain the following compound (a7).

$^1$H-NMR; δ (ppm):
2.51 (2H, t, NHCOCH$_2$CH$_2$), 2.63-2.73 (4H, HCO—CH$_2$CH$_2$—), 3.40-3.90 (1735H, m, —(CH$_2$CH$_2$O)$_n$—CH$_2$, —(CH$_2$CH$_2$O)$_n$—CH, HCO—CH$_2$CH$_2$—, CH$_2$NHCOCH$_2$CH$_2$), 6.70 (2H, 3, CH=CH), 9.80 (2H, HCO—CH$_2$CH$_2$—)

GPC analysis;
number-average molecular weight (Mn): 19,319, weight-average molecular weight (Mw): 20,634, polydispersity (Mw/Mn): 1.068 react at 40° C. for 3 hours. Subsequently, a toluene (256.8 g) solution of 85.6 g (465 mmol) of 3,3-diethoxy-1-propanol containing 2.58 g (112 mmol) of sodium dissolved therein was added thereto and allowed to react at 70° C. for 5 hours. After filtration of the reaction solution, the filtrate was transferred to a 10 L stainless steel pot and crystallization was performed with adding 1,488 g of ethyl acetate, 1,488 g of ethanol, and 2,976 g of hexane. After the precipitated crystals were filtrated to remove the solvents, the crystals were transferred to a 10 L stainless steel pot. After 1,488 g of ethyl acetate and 1,488 g of ethanol were added thereto and heated to dissolve the crystals at 40° C., the solution was cooled to 20° C. and crystallization was performed with adding 2,976 g of hexane. Thereafter, similar crystallization was repeated three times and, after washing with hexane, the crystals were collected by filtration and dried to obtain the following compound (a8).

$^1$H-NMR; δ (ppm):
3.40-3.90 (1728H, m, —(CH$_2$CH$_2$O)$_n$—CH$_2$, —(CH$_2$CH$_2$O)$_n$—CH, CH$_2$O—CH$_2$Ph), 4.54 (2H, s, —CH$_2$Ph), 7.27-7.38 (5H, m, —CH$_2$Ph), 7.65-7.95 (4H, m, Ph(CO)$_2$N—)

GPC analysis;
number-average molecular weight (Mn): 19,398, weight-average molecular weight (Mw): 19,824, polydispersity (Mw/Mn): 1.022

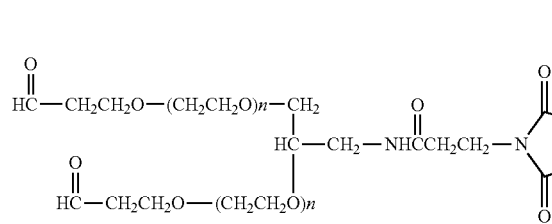

(a7)

$n$ = about 216

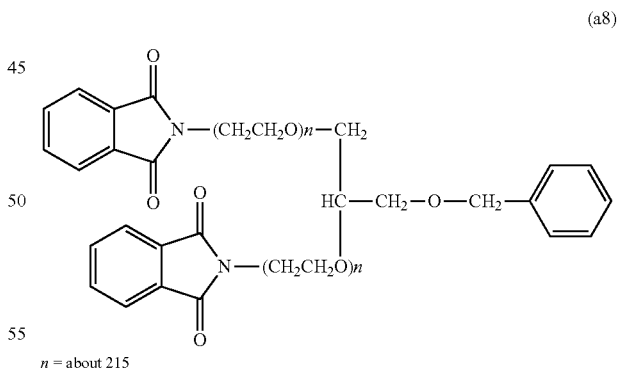

(a8)

$n$ = about 215

Example 8

Into a 1 L four-neck flask fitted with a thermometer, a nitrogen-inlet tube, a stirrer, a Dean-stark tube, and a cooling tube were charged 200 g (10.0 mmol) of the above compound (a1) and 600 g of toluene. The whole was heated under reflux and water was removed as an azeotrope. After cooling to 40° C., 1,000 g of anhydrous chloroform, 8.83 g (60.0 mmol) of phthalimide and 15.7 g (60.0 mmol) of triphenylphosphine were added thereto, followed by stirring and dissolution. After cooling to room temperature, 12.1 g (60.0 mmol) of diisopropylazodicarboxylate was allowed to

Example 9

Into a 1 L four-neck flask fitted with a thermometer, a nitrogen-inlet tube, a stirrer, and a cooling tube were charged 50 g of the above compound (a8) and 25 g of 5% palladium-carbon (a 50% hydrous product). After replacement with nitrogen, 500 g of methanol and 68 g of cyclohexene were added thereto, the temperature was raised, and gentle refluxing was performed at 52 to 55° C. to effect reaction for 5 hours. After cooling of the reaction solution to room temperature, palladium-carbon was filtrated off and the filtrate was concentrated. To the concentrate were added 400 g of toluene and 200 g of hexane, and crystallization was performed. The resulting crystals were collected by filtration and dried to obtain the following compound (a9).

$^1$H-NMR; δ (ppm):
3.40-3.90 (1684H, m, —(CH$_2$CH$_2$O)$_n$—CH$_2$, —(CH$_2$CH$_2$O)$_n$—CH, CH$_2$OH), 7.65-7.95 (4H, m, Ph(CO)$_2$N—)

GPC analysis;
number-average molecular weight (Mn): 18,817, weight-average molecular weight (Mw): 19,171, polydispersity (Mw/Mn): 1.019

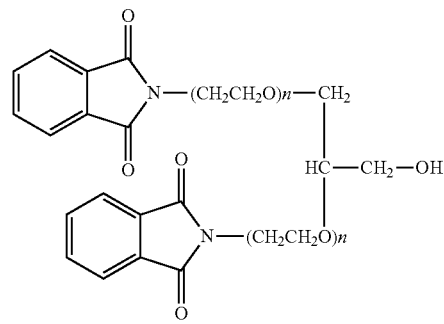

(a9)

$n$ = about 210

Example 10

Into a 1 L four-neck flask fitted with a thermometer, a nitrogen-inlet tube, a stirrer, a Dean-stark tube, and a cooling tube were charged 200 g (10.0 mmol) of the above compound (a1) and 600 g of toluene. The whole was heated under reflux and water was removed as an azeotrope. After cooling to 40° C., 1,000 g of anhydrous chloroform, 8.83 g (60.0 mmol) of phthalimide and 15.7 g (60.0 mmol) of triphenylphosphine were added thereto, followed by stirring and dissolution. After cooling to room temperature, 12.1 g (60.0 mmol) of diisopropylazodicarboxylate was allowed to react at 40° C. for 3 hours. Subsequently, a toluene (256.8 g) solution of 85.6 g (465 mmol) of 3,3-diethoxy-1-propanol containing 2.58 g (112 mmol) of sodium dissolved therein was added thereto and allowed to react at 70° C. for 5 hours. After filtration of the reaction solution, the filtrate was transferred to a 10 L stainless steel pot and crystallization was performed with adding 1,488 g of ethyl acetate, 1,488 g of ethanol, and 2,976 g of hexane. After the precipitated crystals were filtrated to remove the solvents, the crystals were transferred to a 10 L stainless steel pot. After 1,488 g of ethyl acetate and 1,488 g of ethanol were added thereto and heated to dissolve the crystals at 40° C., the solution was cooled to 20° C. and crystallization was performed with adding 2,976 g of hexane. Thereafter, similar crystallization was repeated three times and, after washing with hexane, the crystals were collected by filtration and dried to obtain the following compound (a10).

$^1$H-NMR; δ (ppm):
2.83-2.89 (4H, t, NH$_2$—CH$_2$CH$_2$—), 3.40-3.90 (1676H, m, —(CH$_2$CH$_2$O)$_n$—CH$_2$, —(CH$_2$CH$_2$O)$_n$—CH, CH$_2$OH)

GPC analysis;
number-average molecular weight (Mn): 18,559, weight-average molecular weight (Mw): 19,264, polydispersity (Mw/Mn): 1.038

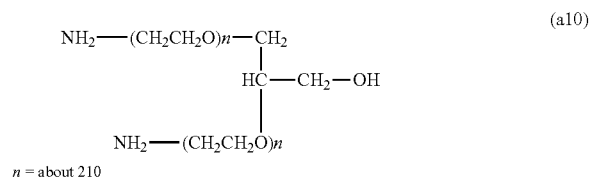

(a10)

$n$ = about 210

Example 11

Into a 100 mL three-neck flask fitted with a thermometer, a nitrogen-inlet tube, a stirrer, a Dean-stark tube, and a cooling tube were charged 5.0 g (0.25 mmol) of the above compound (a5), 26 g of toluene, 4.0 g of acetonitrile, N-methylmorpholine (2.50 mmol), and N-succinimidyl 3-maleimidopropionate (0.75 mmol), followed by reaction at room temperature for 4 hours. After the solution was filtrated, crystallization was performed with adding 100 g of ethyl acetate and 50 g of hexane at room temperature in a 300 mL beaker. Then, after 100 g of ethyl acetate was added and the crystals were dissolved at 40° C., the solution was cooled to room temperature and 100 g of hexane was added to precipitate crystals. After the crystallization was repeated further twice, the crystals were washed with hexane, collected by filtration, and dried to obtain the following compound (a11).

$^1$H-NMR; δ (ppm):
2.51 (2H, t, CH$_2$CH$_2$CONH), 3.40-3.90 (1767H, m, —(CH$_2$CH$_2$O)$_n$—CH$_2$, —(CH$_2$CH$_2$O)$_n$—CH, CH$_2$OH, CH$_2$CH$_2$CONH), 6.50 (1H, s, CH$_2$CH$_2$CONH), 6.70 (2H, s, CH=CH)

GPC analysis;
number-average molecular weight (Mn): 19,734, weight-average molecular weight (Mw): 21,336, polydispersity (Mw/Mn): 1.081

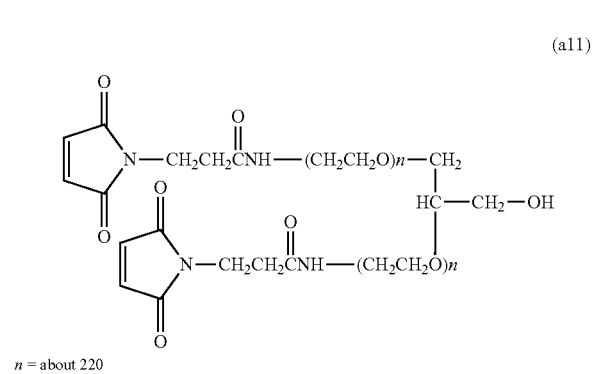

(a11)

$n$ = about 220

Example 12

Into a 100 mL three-neck flask fitted with a thermometer, a nitrogen-inlet tube, a stirrer, a Dean-stark tube, and a cooling tube were charged 4.0 g (0.20 mmol) of the above compound (a5), g of dichloromethane, triethylamine (2.50 mmol), and N,N-disuccinimidyl carbonate (0.75 mmol), followed by reaction at room temperature for 4 hours. After the solution was filtrated and concentrated, crystallization was performed with adding 100 g of ethyl acetate and 50 g of hexane in a 300 mL beaker. Then, after 100 g of ethyl acetate was added and the crystals were dissolved at 40° C., the solution was cooled to room temperature and 100 g of hexane was added to precipitate crystals. After the crystallization was repeated further three times, the crystals were washed with hexane, collected by filtration, and dried to obtain the following compound (a12).

$^1$H-NMR; δ (ppm):
2.51 (2H, t, CH$_2$CH$_2$CONH), 2.84 (4H, s, —CH$_2$O—COO-succinimide), 3.40-3.90 (1751H, m, —(CH$_2$CH$_2$O)$_n$—CH$_2$, —(CH$_2$CH$_2$O)$_n$—CH, —CH$_2$O—COO-succinimide, CH$_2$CH$_2$CONH), 4.36-4.52 (2H, m, —CH$_2$O—COO-succinimide), 6.37 (1H, s, CH$_2$CH$_2$CONH), 6.70 (2H, s, CH=CH)

GPC analysis;
number-average molecular weight (Mn): 19,659, weight-average molecular weight (Mw): 21,450, polydispersity (Mw/Mn): 1.091

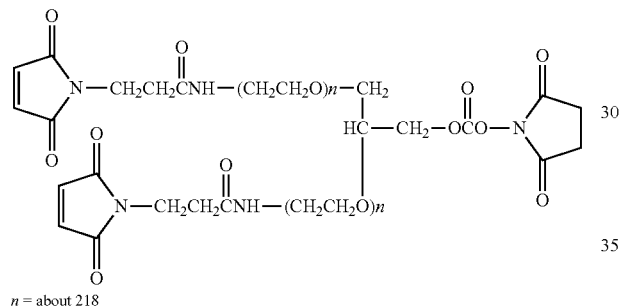

(a12)

n = about 218

Example 13

GRGDS (Gly-Arg-Gly-Asp-Ser, molecular weight: 490.5) was dissolved in an amount of 2.5 mg (5.1 μmol) in 1 ml of 10 mM phosphoric acid buffer (pH=6.4). To 200 μl of the solution was added 10 mg (0.5 μmol) of the compound (a12), and reaction was carried out at room temperature for 1 hour, thereby GRGDS being modified at one active carbonate group in the compound. Subsequently, 20 mg (7.4 μmol) of Humanin (Met-Ala-Pro-Arg-Gly-Phe-Ser-Cys-Leu-Leu-Leu-Leu-Thr-Ser-Glu-Ile-Asp-Leu-Pro-Val-Lys-Arg-Arg-Ala, molecular weight: 2,687.2) was added to the solution, and reaction was carried out at room temperature for 10 hours, thereby Humanin being modified at the two maleimide groups in the compound. Then, 200 μl of the reaction solution was charged onto an SP-Sepharose FF (manufactured by Amersham plc) column and equilibration was performed with 20 mM Tris-HCl buffer (pH 8.2). After equilibration, the buffer to which NaCl had been added so as to be 1N was passed through the column to obtain a fraction of a PEG compound modified with one GRGDS and two Humanin. After 20 μl of the fraction and 20 μl of a Tris SDS sample treating liquid were mixed, the mixture was heated in a boiled water bath for 2 minutes and 30 seconds and 20 μl of the solution was analyzed on sodium dodecyl sulfate-polyacrylamide gel electrophoresis. Staining was performed by CBB staining. As a result, through comparison with respective standard samples, it was shown that a compound where the compound (a12) was modified with one GRGDS and two Humanin.

While the invention has been described in detail with reference to specific embodiments thereof, it will be apparent to one skilled in the art that various changes and modifications can be made therein without departing from the spirit and scope thereof.

The present application is based on Japanese Patent Application No. 2010-145383 filed on Jun. 25, 2010 and Japanese Patent Application No. 2011-070735 filed on Mar. 28, 2011, and the contents are incorporated herein by reference. Also, all the references cited herein are incorporated as a whole.

The invention claimed is:
1. A branched hetero polyethylene glycol represented by the formula [1]:

[1]

wherein X represents an atomic group containing at least a functional group which reacts with a functional group present in a bio-functional molecule to form a covalent bond and Y represents an atomic group consisting essentially of a functional group which reacts with a functional group present in a bio-functional molecule to form a covalent bond and a bonding moiety to be bonded to a branching linker moiety E selected from the group consisting of an ester bond, a urethane bond, an amide bond, an ether bond, a carbonate bond, a saturated hydrocarbon group containing a secondary amino group, a single bond, and a saturated hydrocarbon group, and the functional group contained in the atomic group X and the functional group contained in the atomic group Y are different from each other;
wherein as a combination of the functional group X and the functional group Y:
Y is a group selected from a maleimide group, a vinylsulfone group, an iodoacetamide group, an active carbonate group, an amino group, and an aminoxy group when X is an acetal group,
Y is a group selected from a maleimide group, a vinylsulfone group, an acetylene group, and an azide group when X is an aldehyde group,
Y is a group selected from an acetal group, an active carbonate group, an acetylene group, and an azide group when X is a maleimide group, a vinylsulfone group, or an iodoacetamide group,
Y is a group selected from an acetal group, a maleimide group, a vinylsulfone group, an iodoacetamide group, an acetylene group, and an azide group when X is an active ester group or an active carbonate group,
Y is a group selected from an acetal group, an acetylene group, and an azide group when X is an amino group or an aminoxy group,
Y is a group selected from an acetal group, an aldehyde group, a maleimide group, a vinylsulfone group, an iodoacetamide group, an active ester group, an active carbonate group, an amino group, and an aminoxy group when X is an acetylene group or an azide group,
wherein the active ester group is a group represented by the following formula [9] which is reactive with nucleophilic groups:

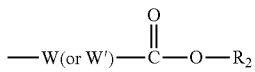
[9]

wherein R₂ is a phenyl group, a 3-pyridyl group, a succinimide group, a 2-benzothiazole group, or a 1-benzotriazole group and W and W' are each independently a linker comprising a covalent bond selected from the group consisting of an ester bond, a urethane bond, an amide bond, an ether bond, a carbonate bond, a saturated hydrocarbon group containing a secondary amino group, a single bond, and a saturated hydrocarbon group;

s is an integer of 2 or 4, which represents a number of polyethylene glycol chains;

n is a number of average added moles for the polyethylene glycol chain and $20 \leq n \leq 2000$; and E is a branching linker moiety represented by the formula [A] or [B]:

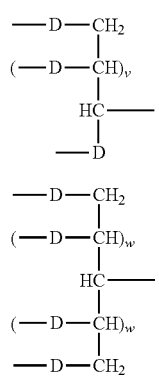

wherein each D is $-(CH_2)_a-O-(CH_2)_b-$, $-(CH_2)_a-O-C(O)-NH-(CH_2)_b-$, $-O-C(O)-NH-(CH_2)_b-$, $-(CH_2)_a-NH-C(O)-O-(CH_2)_b-$, $-(CH_2)_a-C(O)-NH(CH_2)_b$, or $-(CH_2)_a-NH-C(O)-(CH_2)_b$, or a single bond, a=1-12,
b=1-12,
v=0 or 2, and
w=0 or 1.

2. The branched hetero polyethylene glycol according to claim 1, which is represented by the formula [3] or [4]:

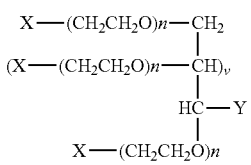

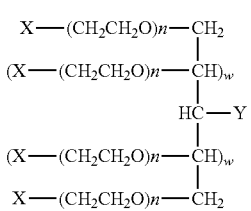

wherein v=0 or 2 and w=0 or 1.

3. The branched hetero polyethylene glycol according to claim 1, wherein as the combination of the functional group X and the functional group Y:

Y is a group selected from a maleimide group, an active carbonate group, an amino group, and an aminoxy group when X is an acetal group, Y is a group selected from an acetal group, an active carbonate group, an acetylene group, and an azide group when X is a maleimide group, Y is a group selected from an acetal group, a maleimide group, an acetylene group, and an azide group when X is an active ester group or an active carbonate group, Y is a group selected from an acetal group, an acetylene group, and an azide group when X is an amino group or an aminoxy group, Y is a group selected from an acetal group, a maleimide group, an active ester group, an active carbonate group, an amino group, and an aminoxy group when X is an acetylene group or an azide group.

* * * * *